(12) United States Patent
Hardy et al.

(10) Patent No.: US 9,880,130 B2
(45) Date of Patent: Jan. 30, 2018

(54) PULSED EDDY CURRENT TESTING WITH DUAL-PURPOSE COILS

(71) Applicant: EDDYFI NDT INC., Québec (CA)

(72) Inventors: Florian Hardy, Saint-Augustin-de-Desmaures (CA); Maxime Rochette, Lévis (CA); Marc Grenier, Québec (CA); Vincent Demers-Carpentier, Québec (CA)

(73) Assignee: EDDYFI NDT INC., Quebec (CA)

( * ) Notice: Subject to any disclaimer, the term of this patent is extended or adjusted under 35 U.S.C. 154(b) by 0 days.

(21) Appl. No.: 15/378,611

(22) Filed: Dec. 14, 2016

(65) Prior Publication Data

US 2017/0168016 A1  Jun. 15, 2017

Related U.S. Application Data (60) Provisional application No. 62/267,470, filed on Dec. 15, 2015.

(51) Int. Cl.
  *G01N 27/90* (2006.01)
  *G01N 27/82* (2006.01)
  *G01N 17/04* (2006.01)

(52) U.S. Cl.
  CPC ......... *G01N 27/9033* (2013.01); *G01N 17/04* (2013.01); *G01N 27/82* (2013.01); *G01N 27/902* (2013.01); *G01N 27/904* (2013.01)

(58) Field of Classification Search
  CPC ................. G01N 27/82; G01N 27/9033
  USPC ................................ 324/240
  See application file for complete search history.

(56) References Cited

U.S. PATENT DOCUMENTS

| | | |
|---|---|---|
| 4,843,319 A | 6/1989 | Lara |
| 5,298,858 A | 3/1994 | Harrison |
| 5,491,409 A | 2/1996 | Flora et al. |
| 6,037,768 A | 3/2000 | Moulder et al. |
| 6,275,030 B1 | 8/2001 | de Haan |
| 6,291,992 B1 | 9/2001 | van Andel et al. |
| 6,344,741 B1 | 2/2002 | Giguere et al. |

(Continued)

FOREIGN PATENT DOCUMENTS

| | | |
|---|---|---|
| CN | 103712637 A | 4/2014 |
| EP | 0376635 A2 | 12/1989 |
| WO | 2010138093 A1 | 12/2010 |

*Primary Examiner* — Reena Aurora
(74) *Attorney, Agent, or Firm* — Fasken Martineau Dumoulin LLP (57) ABSTRACT

A Pulsed Eddy Current device for inspecting an object made of an electrically conductive material comprising: at least one dual-purpose coil serving a dual purpose of producing a supplied magnetic field in the object and measuring a produced magnetic field emitted by the object, a transmitter circuit driving the dual-purpose coil(s) with an electrical signal, a shut-off current circuit for the transmitter circuit for cutting-off a current in the dual-purpose coil(s) during a cut-off phase of the electrical signal, the shut-off current circuit applying a voltage inversion on the dual-purpose coil(s) and a receiver circuit for reading the produced magnetic field from the dual-purpose coil(s). A method for inspecting an object comprising supplying a voltage on at least one dual-purpose coil, cutting-off a current in the dual-purpose coil(s) by applying a voltage inversion on the dual-purpose coil(s) and receiving, at the dual-purpose coil (s), a produced magnetic field.

15 Claims, 9 Drawing Sheets

(56) References Cited

U.S. PATENT DOCUMENTS

| | | |
|---|---|---|
| 6,538,435 B2 | 3/2003 | Crouzen et al. |
| 6,570,379 B2 | 5/2003 | Couzen et al. |
| 6,707,296 B2 | 3/2004 | Looijer |
| 6,720,775 B2 | 4/2004 | Plotnikov et al. |
| 6,911,826 B2 | 6/2005 | Plotnikov et al. |
| 7,389,206 B2 | 6/2008 | Plotnikov |
| 7,402,999 B2 | 7/2008 | Plotnikov et al. |
| 7,508,201 B2 * | 3/2009 | Tada ............... G01B 7/105 324/229 |
| 7,514,918 B2 | 4/2009 | Crouzen |
| 8,079,929 B2 | 12/2011 | Badoux et al. |
| 8,263,409 B2 | 9/2012 | Linder et al. |
| 8,280,690 B2 | 10/2012 | Sobel |
| 8,390,280 B2 | 3/2013 | Badoux et al. |
| 8,547,089 B2 | 10/2013 | De Haan et al. |
| 9,091,664 B2 * | 7/2015 | Krause ............... G01N 27/9053 |
| 2013/0328555 A1 | 12/2013 | Krause et al. |

* cited by examiner

PULSED EDDY CURRENT TESTING WITH DUAL-PURPOSE COILS

FIELD

The present application relates to Pulsed Eddy Current testing and, more particularly, to a nondestructive testing technique with dual-purpose coils.

BACKGROUND OF THE ART

Nondestructive testing (NDT) is a discipline which aims at evaluating the integrity and/or physical properties of materials without permanently altering the object being inspected. There are numerous NDT methods, tailored to various material, component and defect types. Pulsed Eddy Current (PEC) or Transient Eddy Current (TEC) techniques are especially efficient at measuring thickness variations in insulated and/or thick conductive objects. The working principle is to induce transient eddy currents inside the object being inspected by means of a sharp electromagnetic transition and measure its decay to infer material thickness or property changes.

The intensity of the produced magnetic field is proportional to the turn density of the coil and the current passing through it. However, as turn density increases, so does the inductance of the coil. Hence, in most PEC systems, the number of turns in the transmitting coil is kept to a minimum to reduce the inductance of the coil and therefore provide a sudden and/or drastic cutting-off of the coil. Using low inductance transmitting coil ensures that one can measure the magnetic field decay coming from the part without being overly affected by the transmitter coil itself. However, with such a design, generating a sufficiently strong magnetic field requires a very high current, which is not always practical. For example, when the transmitting coil is far from the acquisition instrument and an extension cable is required, significant power losses will ensue in the cable from the Joule effect. Such losses represent a major limitation, especially for a battery-operated instrument.

In contrast, the receiver coil requires very different characteristics to maximize its effectiveness. Its sensitivity will be directly proportional to the number of turns and will not be negatively impacted by the resulting high inductance. This stark difference between the optimal turn density for the transmitting and receiver coils encourages usage of separate sets of coils to prevent a prohibitive loss of performance in prior art systems.

In the context of a compact and portable NDT probe, this represents a major drawback as it increases the amount of components and the footprint they occupy. Additionally, some valuable insight can be gained from measuring the eddy current-produced magnetic field at the exact same position/orientation as the point of transmission. This can prove challenging when using an independent transmitter/receiver system due to potential crosstalk between the two sets of coils. Another downside of having independent sets of transmitters and receivers is that it increases the number of electrical conductors needed to communicate between the probe and the instrument, thus increasing the weight and lowering the flexibility of the electrical cable.

SUMMARY

According to one broad aspect of the present invention, there is provided a Pulsed Eddy Current device for inspecting an object made of an electrically conductive material comprising: at least one dual-purpose coil serving a dual purpose of producing a supplied magnetic field in the object and measuring a produced magnetic field emitted by the object, a transmitter circuit driving the dual-purpose coil(s) with an electrical signal, a shut-off current circuit for the transmitter circuit for cutting-off a current in the dual-purpose coil(s) during a cut-off phase of the electrical signal, the shut-off current circuit applying a voltage inversion on the dual-purpose coil(s); and a receiver circuit for reading the produced magnetic field from the dual-purpose coil(s).

According to another broad aspect of the present invention, there is provided a method for inspecting an object comprising supplying a voltage on at least one dual-purpose coil, cutting-off a current in the dual-purpose coil(s) by applying a voltage inversion on the dual-purpose coil(s) and receiving, at the dual-purpose coil(s), a produced magnetic field.

According to still another broad aspect of the present invention, there is provided a Pulsed Eddy Current device for inspecting an object made of an electrically conductive material comprising: at least one dual-purpose coil, the dual-purpose coil being configured to serve a dual purpose of producing a supplied magnetic field in the object and measuring a produced magnetic field emitted by the object; a transmitter circuit driving the dual-purpose coil with an electrical signal, the transmitter circuit being connected to the dual-purpose coil via at least one electrical conductor, the electrical signal including a transmission phase, a cut-off phase and a reception phase, the transmitter circuit driving the dual-purpose coil to produce the supplied magnetic field and allowing penetration of the supplied magnetic field into the object during the transmission phase; a shut-off current circuit for the transmitter circuit for cutting-off a current in the dual-purpose coil during the cut-off phase of the electrical signal to produce a magnetic field variation which induces eddy currents in the object, the shut-off current circuit applying a voltage inversion on the dual-purpose coil; and a receiver circuit for reading the produced magnetic field from the dual-purpose coil and for generating an inspection signal, the produced magnetic field being produced by the eddy currents in the object and emitted by the object during the reception phase of the electrical signal, the receiver circuit being connected to the dual-purpose coil via the electrical conductor.

In one embodiment, the transmission phase of the electrical signal contains an overdrive voltage phase and a plateau voltage phase.

In one embodiment, the shut-off current circuit includes at least one of a Transient Voltage Suppressor (TVS) and a resistor.

In one embodiment, the device further comprises a current controller circuit for controlling the transmitter circuit into providing the electrical signal.

In one embodiment, the device further comprises a current sensor for reading a current level in the dual-purpose coil and providing the current level to the current controller circuit for adjustment of the electrical signal provided by the transmitter circuit. In one embodiment, the current sensor is a shunt resistor.

In one embodiment, the device further comprises a surge protection circuit for protecting the receiver circuit against an input signal representing said produced magnetic field, the surge protection circuit being adapted to prevent the input signal from reaching the receiver circuit if the input signal has a voltage value greater than a threshold value, said threshold value being lower than an absolute maximum input voltage of the receiver circuit.

In one embodiment, the dual-purpose coil has an overall time constant (L/R) of a same order of magnitude as a time constant of an approximated exponential decay of the supplied magnetic field in the object.

In one embodiment, the device further comprises at least one single-purpose transmitting coil, the single-purpose transmitting coil serving a single purpose of producing an additional supplied magnetic field in the object, the additional supplied magnetic field being combined with the supplied magnetic field.

In one embodiment, the device further comprises at least one magnetic sensor, the magnetic sensor serving a single purpose of measuring the produced magnetic field emitted by the object.

In one embodiment, the device further comprises a probe body, the electrical conductor being sized to allow displacement of the probe body on the object remotely from the transmitter circuit and the receiver circuit, the probe body encasing the dual-purpose coil and the shut-off current circuit.

In one embodiment, the device further comprises a plurality of the dual-purpose coil are assembled in an array, each one of the plurality measuring the produced magnetic field emitted by the object, the transmitter circuit driving each one of the plurality in one of a simultaneous mode and a time-multiplexed mode, wherein the transmitter circuit drives each of the dual-purpose coil of the plurality simultaneously in the simultaneous mode and wherein the transmitter circuit drives selected ones of the dual-purpose coil of the plurality simultaneously at each time instance in the time-multiplexed mode.

In one embodiment, the plurality of the dual-purpose coil is assembled on one of a U-shaped core, a three-pronged core, a matrix core and a zigzag-shaped core.

According to yet another broad aspect of the present invention, there is provided a method for inspecting an object made of an electrically conductive material by Pulsed Eddy Current measurement comprising: supplying a voltage on at least one dual-purpose coil by a transmitter circuit during a transmission phase of an electrical signal to drive the dual-purpose coil to produce a supplied magnetic field in the object; cutting-off a current in the dual-purpose coil during a cut-off phase of said electrical signal to produce a magnetic field variation which induces eddy currents in the object, the cutting-off being carried out by applying a voltage inversion on the dual-purpose coil; receiving a produced magnetic field by the dual-purpose coil during a reception phase of said electrical signal, the produced magnetic field being produced by the eddy currents in the object; and outputting an inspection signal by a receiver circuit, the inspection signal being representative of the produced magnetic field in the object received by the dual-purpose coil.

In one embodiment, the method further comprises reading a current level in the dual-purpose coil and adjusting the electrical signal using the current level.

BRIEF DESCRIPTION OF THE DRAWINGS

Further features and advantages of the present invention will become apparent from the following detailed description, taken in combination with the appended drawings, in which:

FIG. 1 includes FIG. 1A (Prior Art), FIG. 1B and FIG. 1C in which

FIG. 2 includes FIG. 2A (Prior Art), FIG. 2B (Prior Art) and FIG. 2C in which

FIG. 3 includes FIG. 3A, FIG. 3B and FIG. 3C in which

FIG. 4 includes FIG. 4A and FIG. 4B in which

FIG. 5 includes FIG. 5A and FIG. 5B in which

FIG. 7 includes FIG. 7A and FIG. 7B in which

FIG. 8 includes FIG. 8A, FIG. 8B, FIG. 8C and FIG. 8D in which

FIG. 9 includes FIG. 9A and FIG. 9B in which FIG. 10 includes FIG. 10A and FIG. 10B in which

It will be noted that throughout the appended drawings, like features are identified by like reference numerals.

DETAILED DESCRIPTION

Figure 1A:
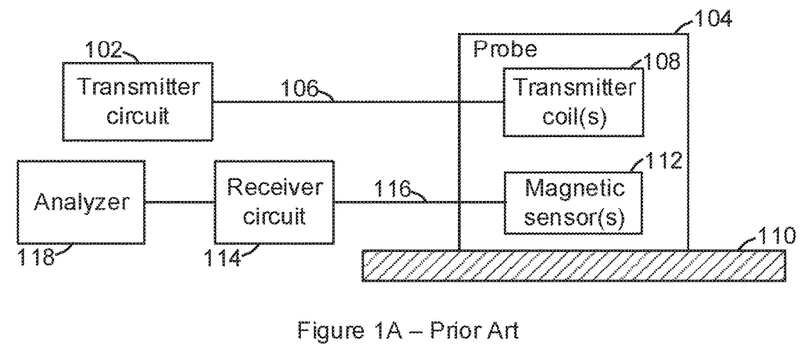
FIG. 1A is a block diagram of a prior art Pulsed Eddy Current probe system.

FIG. 1A shows the prior art technology for a Pulsed Eddy Current (PEC) device used for the detection and measurement of surface and sub-surface corrosion in an electrically conductive material, such as a metallic material. It includes a transmitter circuit 102 linked to a probe 104 by at least one electrical conductor 106. The electrical conductor 106 is connected to at least one transmitter coil 108 located in the probe 104 to produce a magnetic field in the object 110 being inspected. The probe 104 also includes at least one magnetic sensor 112 linked to a receiver circuit 114 by at least one other electrical conductor 116. The magnetic sensor 112 is used to measure the magnetic field emitted by the object 110 being inspected. The receiver circuit 114 may carry out signal conditioning before transmitting the signal to the analyzer 118. The analyzer 118 is responsible for extracting specific information about the object 110 being inspected such as wall loss, liftoff variations and/or local material properties change by applying specialized algorithms to the signal.

Figure 1B:
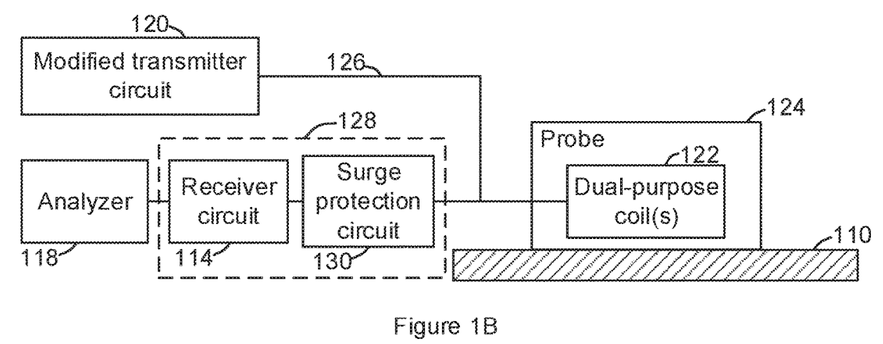
FIG. 1B is a block diagram of a Pulsed Eddy Current device using dual-purpose coil(s) and FIG. 1C is a block diagram of a pulsed Eddy Current device using dual-purpose coil(s), prior art transmitter coil(s) and prior art magnetic sensor(s)

The device shown in FIG. 1B is also a Pulsed Eddy Current (PEC) device used for the detection and measurement of surface and sub-surface corrosion in an electrically conductive material. It includes a modified transmitter circuit 120 linked to at least one dual-purpose coil 122 located in the probe 124 by at least one electrical conductor 126. The dual-purpose coil 122 is also linked to a modified receiver circuit 128 by the same electrical conductor 126. This allows the dual-purpose coil 122 to serve the dual purpose of: a) producing a supplied magnetic field in the object 110 being inspected and b) measuring the produced magnetic field emitted by the object 110 being inspected. The modified reception circuit 128 may include a surge protection circuit 130 to prevent the voltage present on electrical conductor 126 from damaging the receiver circuit 114. The receiver circuit 114 may carry out signal conditioning before transmitting the signal to the analyzer 118.

The Pulsed Eddy Current device for inspecting an object made of an electrically conductive material can be summarized as comprising at least one dual-purpose coil 122, a transmitter circuit 120 driving the dual-purpose coil(s) 122 with an electrical signal, a shut-off current circuit for the transmitter circuit and included in the modified transmitter circuit 120 for cutting-off a current in the dual-purpose coil(s) by applying a voltage inversion on the dual-purpose coils 122 and a receiver circuit 114 for reading the produced magnetic field from the dual-purpose coil(s). The receiver circuit 114 reads the produced magnetic field from the dual-purpose coil(s) and generates an inspection signal.

The body of the probe 104 encases the dual-purpose coil(s) and is adapted for displacement on the object to be inspected. The body of the probe 104 could optionally also encase the shut-off current circuit which is illustrated as part of the modified transmitter circuit 120 on FIG. 1B. The electrical conductor(s) 126 for this probe 104 are sized to allow displacement of the probe body on the object remotely from the modified transmitter circuit 120 and the modified receiver circuit 128.

Figure 1C:
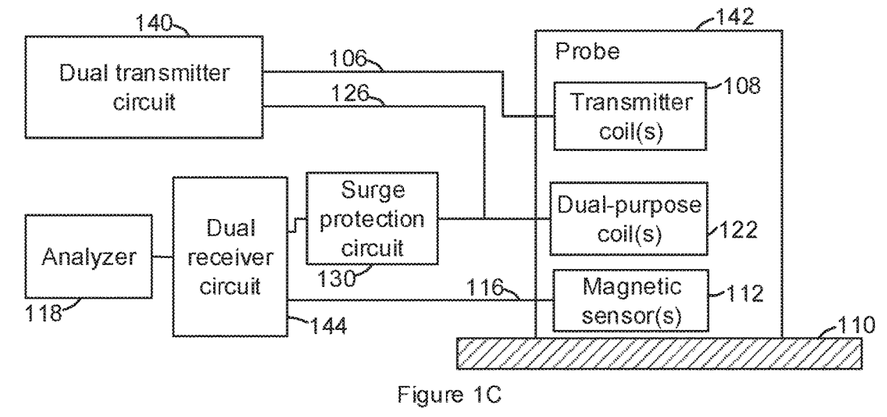

Dual-purpose coil 122 can be used in combination with single-purpose magnetic field transmitter(s) and/or receiving magnetic sensor(s) to expand its functionality. The device shown in FIG. 1C is another Pulsed Eddy Current (PEC) device used for the detection and measurement of surface and sub-surface corrosion in an object 110 made of a conductive material. The probe includes at least one dual-purpose coil, at least one single-purpose magnetic field transmitter and at least one receiving magnetic sensor. Dual transmitter circuit 140 is linked to at least one dual-purpose coil 122 located in the probe 142 by at least one electrical conductor 126. The dual-purpose coil 122 is also linked to a dual receiver circuit 144 and the surge protection circuit 130 by the same electrical conductor 126. The probe 142 also includes transmitter coil 108 linked to the dual transmitter coil 140 by at least one electrical conductor 106. Probe 142 includes a magnetic sensor 112 linked to dual receiver circuit 144 by at least one conductor 116. The receiver circuit 114 may carry out signal conditioning before transmitting the inspection signal to the analyzer 118. As will be readily understood, other embodiments could be made in which the probe contains dual-purpose coil(s) and single-purpose transmitter coil(s) but does not include magnetic sensor(s) or, inversely, in which the probe contains dual-purpose coil(s) and magnetic sensor(s) without single-purpose transmitter coil(s). The single-purpose transmitting coil(s) serve a single purpose of producing an additional supplied magnetic field in the object. The additional supplied magnetic field is combined with the supplied magnetic field of the dual-purpose coil(s). Each of the magnetic sensor(s) serves a single purpose of measuring the produced magnetic field emitted by the object.

Figure 2A:
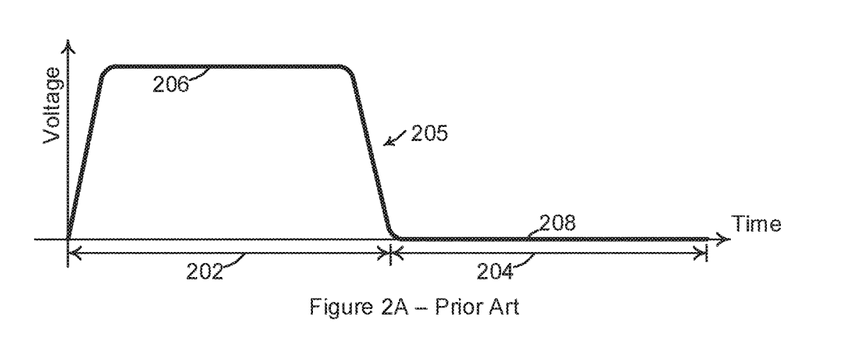
FIG. 2A shows the typical electrical signal provided by the prior art transmitter circuit to the transmitter coil via the electrical conductor.

FIG. 2A shows the typical electrical signal 205 provided, in the prior art, by the transmitter circuit 102 to the transmitter coil 108 via the electrical conductor 106. It is divided in two phases: transmission phase 202 and reception phase 204. During the transmission phase 202, the transmitter circuit 102 supplies a step voltage 206 to the transmitter coil 108 to produce a magnetic field. The transmission phase 202 duration is set long enough to allow deep penetration of the magnetic field into the object 110 being inspected. The reception phase 204 follows the transmission phase 202 and the voltage supplied to the transmitting coil 108 is set to zero 208. The decay of the current in the transmitter coil 108, following the end of the transmission phase 202, occurs during the reception phase 204 and produces an unwanted magnetic field.

Figure 2B:
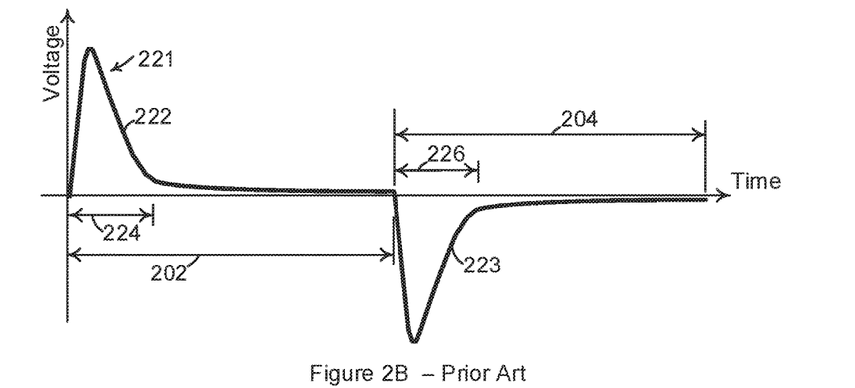
FIG. 2B shows the typical electrical signal received from a magnetic sensor by the electrical conductor in the prior art system depicted in FIG. 1A

FIG. 2B shows the typical electrical signal 221 received from at least one magnetic sensor 112 by the electrical conductor 116 in prior art systems. In both the transmission phase 202 and the reception phase 204, the received signal 221 is a combination of the response from the transmitter coil 108, in charging and discharging modes, and the response from the object 110 being inspected. This latter response is the one of interest for this application. However, the early portions 222, 223 of the received signal 221 as shown in phases 224 and 226 tend to be dominated by the magnetic field variation emitted from the transmitter coil 108 which blinds the signal of interest in the prior art systems.

Figure 2C:
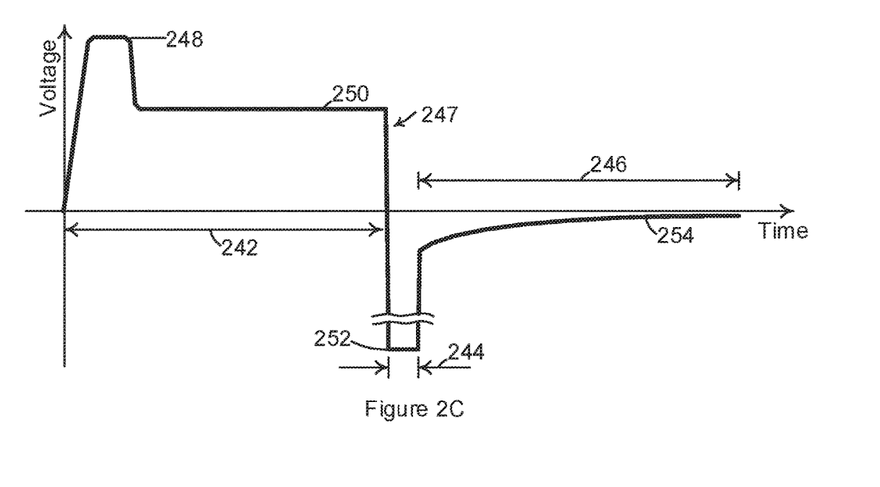
FIG. 2C shows the electrical signal injected in the electrical conductor in the system of FIG. 1B.

FIG. 2C shows the electrical signal 247 injected in the electrical conductor 126 in the system of FIG. 1B. It is divided in three successive phases: transmission phase 242, cut-off phase 244 and reception phase 246.

During the transmission phase 242, the modified transmitter circuit 120 supplies the voltage applied on the dual-purpose coil 122 through the electrical conductor 126. The applied voltage produces a current in the dual-purpose coil 122 which in turn produces a magnetic field in the object 110 being inspected. In order to produce an intense magnetic field, the dual-purpose coil 122 needs to have a high turn density and hence a high inductance. This high inductance leads to a longer time to establish the current in the dual-purpose coil 122. To offset this effect, an overdrive voltage 248 may be applied by the modified transmitter circuit 120. The overdrive voltage 248 is maintained until the desired current is reached. Then, the voltage is reduced to a plateau level voltage 250 to maintain the current to the desired level.

During the transmission phase 242, eddy currents are induced into the object 110 being inspected. At the beginning of the transmission phase 242, these eddy currents block the magnetic field from going into the object 110 being inspected. As is known in the art, the eddy currents gradually decay and the magnetic field penetrates the object 110 being inspected. For optimal performances, a person skilled in the art adjust the transmission phase 242 duration to be long enough to allow the magnetic field to be established homogeneously through the object 110 being inspected.

The cut-off phase 244 follows the transmission phase 242 and is used to suddenly and/or drastically cut off the current in the dual-purpose coil 122 to produce a magnetic field variation which induces eddy currents in the object 110 being inspected. In some applications, a sharp magnetic field variation yield better results. To allow such a drastic current cut-off in the dual-purpose coil 122, the modified transmitter circuit 120 supplies a voltage inversion 252 to the dual-purpose coil 122 through the electrical conductor 126. This voltage inversion 252 may be a high voltage inversion which causes a sufficiently rapid cut-off in the dual-purpose coil 122 to discern the whole frequency response of the material. The surge protection circuit 130 protects the receiver circuit 114 against the high voltage inversion 252. The cut-off phase 244 lasts up to the point where there is no more current flowing in the dual-purpose coil 122. The cut-off phase 244 ensures that even with a high time constant (inductance over resistance, L/R), the decay of the signal from the transmission phase 242 does not leak into the reception phase 246.

The reception phase 246, which follows the cut-off phase 244, corresponds to the phase where the modified transmitter circuit 120 is no longer active and is set to high output impedance. During the reception phase 246, the dual-purpose coil 122 receives the magnetic field from the object 110 being inspected and produces an input signal 254 read by the receiver circuit 114. The receiver circuit 114 produces an inspection signal.

The dual-purpose coils play the dual role of transmitter and receiver which reduces the number of coils necessary in the probe. This can improve the probe weight, footprint and, in some cases, can allow for more precise magnetic field measurements while also improving the weight and flexibility of the electrical cable between the probe and the instrument.

The above description of FIG. 2 is qualitative since many factors will influence the design choices made by the person skilled in the art at the time of creating a specific device. Even though these factors are well known in the art, a description of the compromises required at the time of design follows with some example values.

The exponential decay time constant of the object being inspected should be obtained prior to the design of a PEC inspection device. As will be readily understood by the person skilled in the art, the exponential decay time constant of the object being inspected depends mainly on the permeability, conductivity and thickness of the electrically conductive material. For example, tests were made on various carbon steel alloys. An exponential decay time of 0.7 ms was obtained for a 3 mm thick object and an exponential decay time of 2 s was obtained for an object having a thickness of 100 mm.

During the transmission phase 242, some eddy currents are induced in the object. These eddy currents oppose the deep penetration of the magnetic field in the object. The homogeneity of the magnetic field penetration improves with the transmission phase 242 duration while the inspection speed decreases with the transmission phase 242 duration. The person skilled in the art determines the pulse duration based on the best compromise between the magnetic field penetration homogeneity and the inspection speed. In many cases, the best compromise on the transmission phase 242 duration is between two to six times the exponential decay time of the object.

The cut-off phase 244 duration limits the frequency contents of the received signal during the reception phase 246. A shorter cut-off phase duration allows higher signal frequency contents. The frequency contents of the signal are also linked to the exponential decay time constant of the object. Typically, the cut-off phase 244 duration should be in the range of 0.1 to 1 times the exponential decay time constant of the object. The cut-off phase 244 duration could be estimated with the following formula:

$$CutOffPhaseDuration = \left| \frac{Inductance \times Current}{VoltageInversion} \right|$$

where,

CutOffPhaseDuration is the estimated duration, in seconds, of the cut-off phase 244.

Inductance is the inductance, in Henrys, of the coil(s) used to transmit magnetic field during the transmission phase 242.

Current is the current, in Amperes, in the coil(s) used to transmit magnetic field during the transmission phase 242, at the end of the transmission phase 242.

VoltageInversion is the voltage inversion, in volts, applied on the coil(s) used to transmit magnetic field during the transmission phase 242, during the cut-off phase 244.

A higher inductance and a higher current increase the magnetic field intensity penetrating in the object which in turn increases signal sensitivity and improves the signal-to-noise ratio. Voltage inversion should be limited to prevent damage, in particular damage on the insulation of the winding of the coil(s). The person skilled in the art determines the best compromise between the cut-off phase 244 duration, the inductance of coil(s) used to transmit magnetic field and the voltage inversion magnitude. Other constrains such as probe size and weight limitations and the probe heat dissipation capacity should be taken into account. The person skilled in the art may elect to reduce the current to avoid overheating of the probe and reduce the inductance of the coil(s) to reduce the size and weight of the probe. Typically, a voltage inversion in the range of 50 to 200 V is a good compromise to prevent damage and reduce the cut-off phase duration. The inductance of the coil(s), in Henrys, used to transmit magnetic field is typically set in the range of 5 to 50 times the exponential decay time constant, in seconds, of the object. For example, an inductance of 10 mH might be used to inspect an object having an exponential decay time constant of 1 ms.

Referring back to FIG. 1B and to FIG. 2C, a method for inspecting an object made of an electrically conductive material by Pulsed Eddy Current measurement can be understood. The method comprises supplying a voltage on at least one dual-purpose coil by a transmitter circuit during a transmission phase of an electrical signal to drive the dual-purpose coil(s) to produce a supplied magnetic field in the object; cutting-off a current in the dual-purpose coil(s) during a cut-off phase of the electrical signal to produce a magnetic field variation which induces eddy currents in the object, the cutting-off being carried out by applying a voltage inversion on the dual-purpose coil(s); receiving a produced magnetic field by the dual-purpose coil(s) during a reception phase of the electrical signal, the produced magnetic field being produced by the eddy currents in the object and emitted by the object; and outputting an inspection signal by a receiver circuit, the inspection signal being representative of the produced magnetic field in the object received by the dual-purpose coil(s). The method can further include reading a current level in the dual-purpose coil(s) and adjusting the electrical signal using the current level.

Figure 3A:
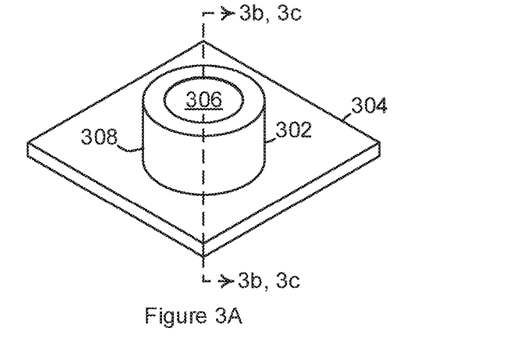
FIG. 3A shows an example of a dual-purpose coil positioned on an object being inspected.

FIG. 3A shows an example of a dual-purpose coil 302 positioned on an object 304 being inspected. In this configuration, the dual-purpose coil 302 is used as a magnetic field transmitter as well as a magnetic field sensor. The core 306 positioned in the center of the winding 308 of the dual-purpose coil 302 could be either a non-ferromagnetic or ferromagnetic component. A ferromagnetic core raises the inductance of the coil which increases the magnetic field emitted by the dual-purpose coil 302.

Figure 3B:
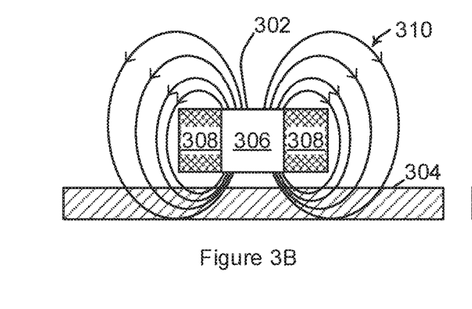
FIG. 3B shows a cross section view of the dual-purpose coil of FIG. 3A with the magnetic field represented as it is at the end of the transmission phase and FIG. 3C shows a cross section view of the dual-purpose coil of FIG. 3A during the reception phase.

FIG. 3B shows a cross section view of the dual-purpose coil 302 of FIG. 3A with the magnetic field represented as it is at the end of the transmission phase 242. The dual-purpose coil 302 produces a magnetic field which increases with the turn density and the current supplied. The magnetic field lines 310 propagate through the object 304 being inspected, magnetizing it over the whole thickness, if the transmission phase 242 is sufficiently long, and looping back onto themselves following Gauss's law for magnetism.

Figure 3C:
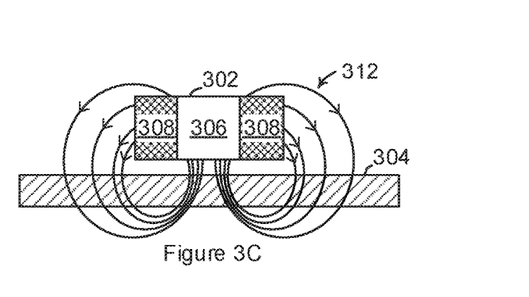

FIG. 3C shows a cross section view of the dual-purpose coil 302 of FIG. 3A during the reception phase 246. At this time, the dual-purpose coil 302 serves as a magnetic field sensor. Following the cut-off phase 244, some eddy currents are induced in the object 304 being inspected to compensate the loss of magnetic energy. These slowly decaying eddy currents produce magnetic field lines 312 which are sensed with the dual-purpose coil 302.

Figure 4A:
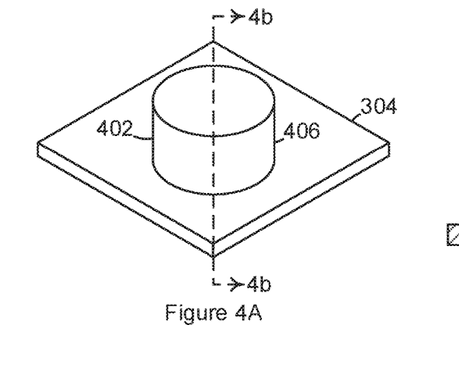
FIG. 4A shows another example of a dual-purpose coil positioned on an object being inspected and FIG. 4B shows a cross section view of the dual-purpose coil of FIG. 4A.
Figure 4B:
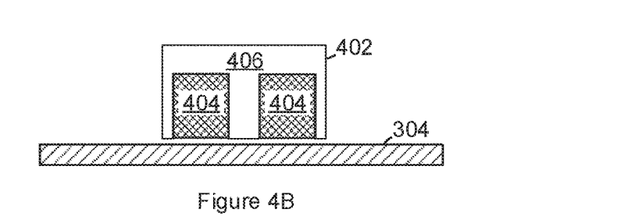

FIGS. 4A and 4B show a dual-purpose coil 402 made of a winding 404 encased in a pot core 406 made of ferromagnetic or non-ferromagnetic material. A ferromagnetic pot core 406 would increase the inductance of the dual-purpose coil 402 and hence increase the intensity of the magnetic field generated as well as better orient the magnetic field toward the object 304 being inspected.

Figure 5A:
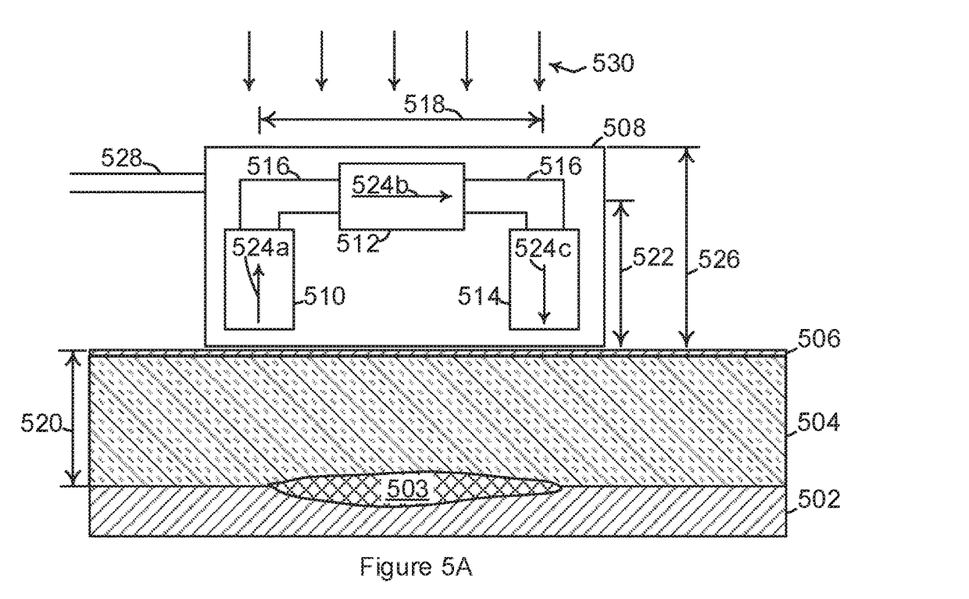
FIG. 5A shows an example of a probe for the inspection of an object and FIG. 5B shows two examples of received signals from the dual-purpose coils during the reception phase.

FIG. 5A shows an example probe for the inspection of an object. The probe is used to inspect an object 502 made of an electrically conductive material which includes corrosion 503. The object 502 is covered with insulation material 504 and a metallic weather jacket 506. The probe 508 has a probe body which is positioned over the metallic weather jacket 506.

The probe 508 includes three coils 510, 512 and 514 mounted on a U-shaped support core 516. Support core 516 can be ferromagnetic or not. The three coils 510, 512 and 514 are used to transmit magnetic field during the transmission phase 242. The polarity of each coil 510, 512 and 514 is set to obtain the magnetic field direction as indicated by arrows 524a, 524b and 524c, collectively referred to as arrows 524.

For the reception phase 246, the probe 508 can have a plurality of magnetic sensor configurations including series connection of coils 510, 512 and 514 providing optimal signal transmission and reception. In this series connection which follows the configuration of FIG. 1B, all coils 510, 512 and 514 are dual-purpose coils. Alternatively, a combination of single purpose and dual-purpose coils could be used in the same probe 142. This is illustrated in FIG. 1C. For example, coils 510 and 514 could be used as dual-purpose coils 122 with coil 512 used as a single purpose transmitting coil 108. As shown by the magnetic field directions 524a and 524c, dual-purpose coil 510 and 514 are in antiparallel configuration. This antiparallel configuration improves the noise immunity due to the fact that the parasitic external magnetic field 530 tends to induce opposite noise voltage in each dual-purpose coil 510 and 514 which is cancelled when the signal from both dual-purpose coil 510 and 514 are summed together. In another example, coil 512 is used as a dual-purpose coil 122 while coils 510 and 514 are used as single purpose receiver coils 112.

The center-to-center distance 518 between the coils 510 and 514 used as dual-purpose coils influences the probe performance. If the distance 518 is too small, the magnetic field will be concentrated close to the probe and the amount of magnetic field reaching the object 502 will be low which might cause a poor signal quality. On the other hand, if the distance 518 is too large, the magnetic field generated by the probe will spread too wide, resulting in poor spatial resolution and limiting the signal contribution of small flaws. A person skilled in the art will determine the optimal distance 518 to obtain satisfactory results depending on the application. FIG. 5A shows an example where the distance 518 has been set at twice the total thickness 520 of the insulation material 504 and the weather jacket 506. The distance 522 between the bottom of the probe 508 and the center of coil 512 should be also optimized by a person skilled in the art. A consequence of the coils 510 and 514 being too short is that the magnetic field they generate could loop back on itself without reaching the object 502 through the thickness 520.

Figure 5B:
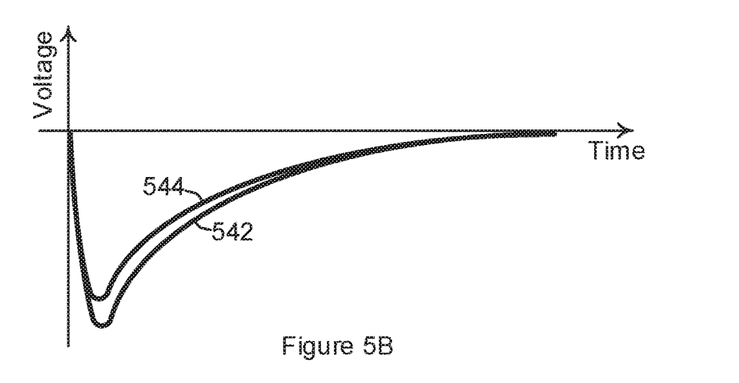

FIG. 5B shows two examples of the signal received from three coils 510, 512 and 514 used as dual-purpose coils during the reception phase 246. Received signal 542 is obtained from the assembly shown in FIG. 5A. Received signal 544 is obtained from a modified version of the assembly of FIG. 5A in which the metallic weather jacket 506 has been removed. The signal difference is caused by the fact that eddy currents are induced into the metallic weather jacket 506 which absorbs some energy and causes some delay on the signal. The received signals 542 and 544 quickly reach a negative voltage peak and then slowly return to 0 V in what can be approximated as an exponential decay whose time constant is correlated with the wall thickness of the object 502.

The optimal inductance and resistance of the winding of the coils can be determined by the person skilled in the art. Raising the inductance increases the transmitted magnetic field intensity which improves the signal-to-noise ratio. The drawbacks of raising the inductance are the increase of the probe weight and size due to the number of winding turns increase and the inspection time increase due to the longer transmit current establishment time in the dual-purpose coil 302 or of a series connection of coils 510, 512, 514 used as dual-purpose coils during the transmission phase 242. Lowering the resistance of the winding reduces the power lost by Joule effect which helps to reduce the probe temperature increase and to save energy (a factor to consider for battery-operated equipment). The resistance of the winding is decreased by increasing the wire gauge size which increases the probe size and the probe weight.

In an example embodiment, the effective time constant (L/R) of the winding is of the same order of magnitude as the time constant of the approximated exponential decay of the received signal 542 or 544 or of the supplied magnetic field in the object. This typically represents a good compromise where the inspection time is not overly increased by the time constant of the winding.

Figure 6:
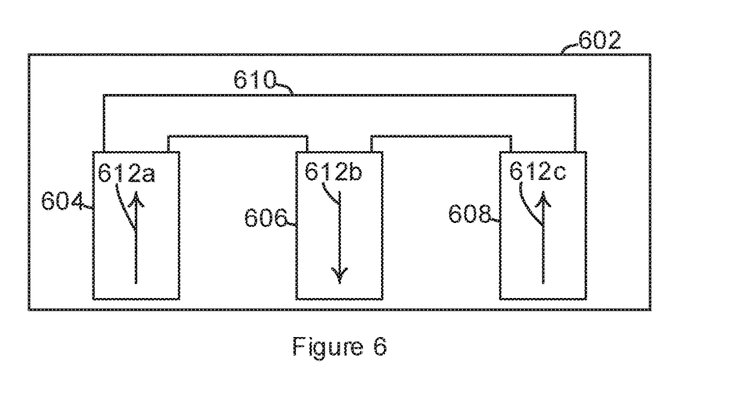
FIG. 6 shows another example of a probe with a configuration that includes three dual-purpose coils and a support core.

FIG. 6 shows another example probe 602 with a configuration that includes three dual-purpose coils 604, 606 and 608 and a support core 610. Support core 610 can be made of a ferromagnetic material or not. Dual-purpose coils 604, 606 and 608 are generally arranged in a three-pronged configuration. The polarity of each coil 604, 606 and 608 is set to obtain the magnetic field direction as indicated by arrows 612*a*, 612*b* and 612*c*, collectively referred to as arrows 612, to create a more intense magnetic field in the center dual-purpose coil 606.

Figure 7A:
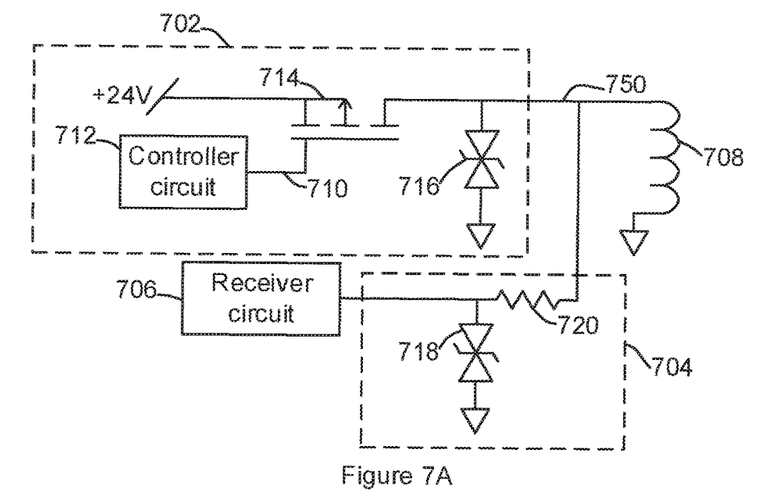
FIG. 7A shows an example fast shut-off current circuit with a high voltage receiver input surge protection circuit and FIG. 7B shows another example fast shut-off current circuit with a high voltage receiver input surge protection circuit.

FIG. 7A shows an example fast shut-off current circuit with a high voltage receiver input surge protection circuit. A fast shut-off current 24 V transmitter circuit 702 is provided with a high voltage receiver input surge protection circuit 704 used with a receiver circuit 706 and a dual-purpose coil 708. The phase control signal 710, supplied by the controller circuit 712, controls the p-channel field-effect transistor (FET) 714. The current controller circuit 712 is for controlling the transmitter circuit 702 into providing the electrical signal. The phase control signal 710 is set at the right voltage to make the FET 714 conductive, which brings a voltage of 24 V minus a small voltage drop in the FET 714 and on the conductor 750 to the dual-purpose coil 708 during the transmission phase 242. During the transmission phase 242, the current in the dual-purpose coil 708 increases gradually. At the end of the transmission phase 242, the FET 714 is set back to non-conductive by the phase control signal 710 change.

During the cut-off phase 244, the dual-purpose coil 708 produces an inverse voltage as it tries to maintain its current. This inverse voltage reaches the Transient Voltage Suppressor (TVS) 716 conduction voltage, which is for example −100 V. The inverse voltage produces a rapid current decay in the dual-purpose coil 708. The current decay rate depends on the level of the inverse voltage. The voltage on conductor 750 could damage the receiver circuit 706 which is often designed to resist a much lower voltage. To avoid receiver circuit 706 damage, the voltage on conductor 750 is sent to the receiver circuit 706 via the surge protection circuit 704. The TVS 718 conduction voltage is lower than the maximum voltage that the receiver circuit 706 can accept without damage. The surge protection circuit 704 is provided for protecting the receiver circuit 706 against a signal representing the produced magnetic field which would be higher than a threshold value. This threshold value is determined by the person skilled in the art and is lower than an absolute maximum input voltage of the receiver circuit 706.

For example, a person skilled in the art may select a TVS 718 model having the conducting voltage at ±5 V to protect a receiver circuit 706 that can accept ±8 V input. The resistor 720 is selected to limit the current from the dual-purpose coil 708. In this example, the resistor 720 is set at 1 kΩ and it drains 95 mA when the TVS 716 is in conduction. When the current in the dual-purpose coil 708 decreases below 95 mA the TVS 716 stops conducting and the inverse voltage starts dropping which slows the current drop rate in the dual-purpose coil 708. The inverse voltage is produced by the dual-purpose coil 708 up to the point when its current drops to 0 A. At that point, the cut-off phase 244 is finished and the reception phase 246 starts.

During the reception phase 246, the voltage produced by the dual-purpose coil 708 is proportional to the variation of magnetic field transmitted by the object being inspected. An inspection signal is generated by the receiver circuit 706.

Figure 7B:
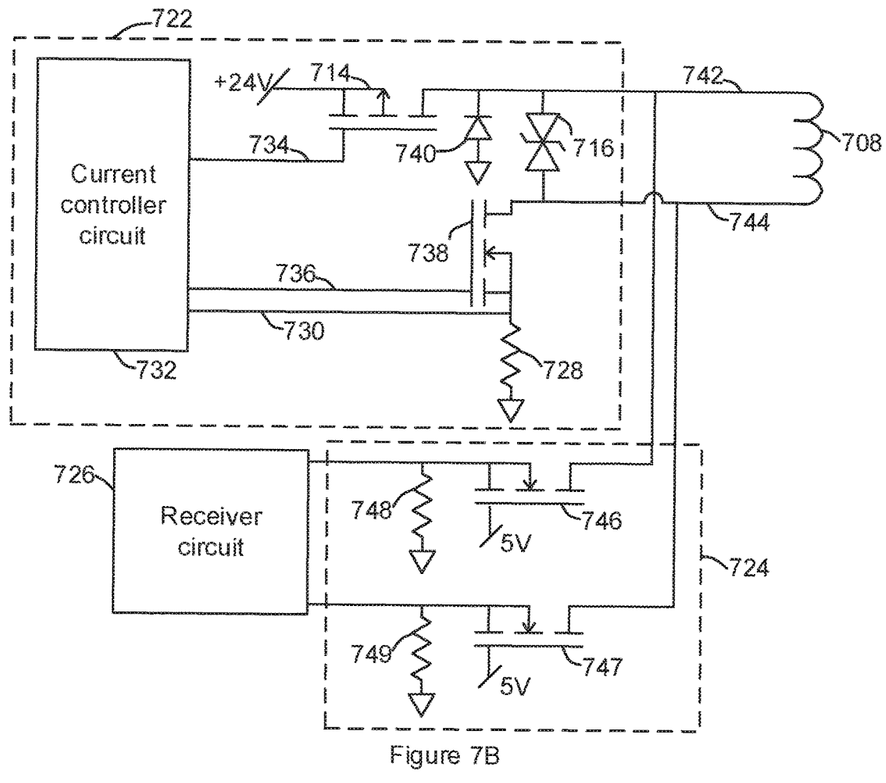

FIG. 7B shows another example of a fast shut-off current circuit with a high voltage receiver input surge protection circuit. Fast shut-off current transmitter circuit 722 is provided with a high voltage receiver input surge protection circuit 724 and both are used with a differential input receiver circuit 726 and a dual-purpose coil 708. The transmitter circuit 722 provides a current source to the dual-purpose coil 708 during the transmission phase 242 through the FET 714. The shunt resistor 728 is used to read the current in the dual-purpose coil 708. The current sensed signal 730 at the shunt resistor 728 is used as feedback to the transmitter current controller circuit 732. The shunt resistor is therefore used as a current sensor for reading a current level in the dual-purpose coil and providing the current level to the current controller circuit for adjustment of the electrical signal provided by the transmitter circuit. The current control signal 734 issued from the current controller circuit 732 is used to set the conduction level of the FET 714 to get the desired current in the dual-purpose coil 708 during the transmission phase 242. During the transmission phase 242, the transmitter control circuit provides the phase control signal 736 to the n-channel FET 738 to make it conductive.

The person skilled in the art will select the resistor value of the shunt resistor 728 small enough to reduce the power lost and large enough to get significant current signal amplitude. For example, 0.1Ω might be a good compromise for the shunt resistor 728 value.

During the cut-off phase, the current controller circuit 732 sets the phase control signal 736 to make the FET 738 nonconductive and the current control signal 734 to make the FET 714 nonconductive. The dual-purpose coil 708 produces an inverse voltage trying to keep its current. This inverse voltage reaches the conduction voltage of the TVS 716 and makes it conductive. The diode 740 is conductive if the voltage at the point 742 becomes negative. The voltage at the point 744 goes up to about 100 V which is the conductive voltage of the TVS 716. The voltages at the points 742 and 744 are sent to the differential input receiver circuit 726 through the receiver input surge protection circuit 724.

During the transmission phase 242, the voltage at point 742 may reach 24 V and during the cut-off phase, the voltage at point 744 may reach 100 V which could damage the receiver circuit 726 if it was directly connected to these points 742 and 744 and did not already include an internal surge protection system.

The receiver input surge protection circuit 724 is made of two n-channel FET 746, 747 which are conductive if their gate voltage is higher than their source voltage plus their voltage gate-source threshold. The value of resistors 748, 749 is for example set at 100 kΩ and this therefore limits the current to 45 µA while the receiver input voltage will be limited to +4.5 V if the FET 746, 747 conductive gate-source threshold is 0.5 V. As will be readily understood, FET 746 and FET 747 could be identical in some embodiments. As will also be understood, resistor 748 and resistor 749 could be identical in some embodiments.

When more than one dual-purpose coil is provided in the probe, the coils can be arranged in arrays. The transmitter circuit drives each coil of the array either in simultaneous mode or in a time-multiplexed mode. In the simultaneous mode, all coils are driven simultaneously. In the time-multiplexed mode, the transmitter circuit drives selected coils simultaneously at each time instance in the time-multiplexed mode according to a pattern. Each coil measures the produced magnetic field emitted by the object. The coils can be assembled on a variety of supports and cores, such as a U-shaped core, a three-pronged core, a matrix core or a zigzag-shaped core.

Figure 8A:
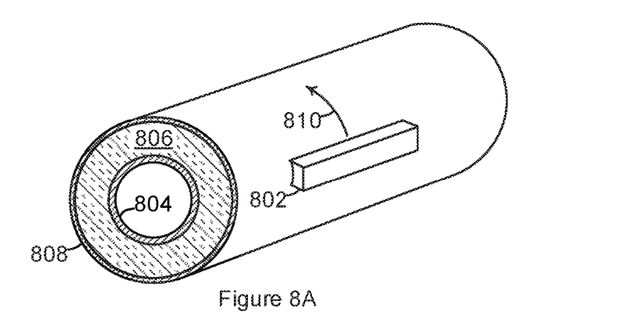
FIG. 8A shows an example of a longitudinal array probe positioned on a pipe, the length of the array probe being along the longitudinal dimension of the pipe.

FIG. 8A shows an example of a Pulsed Eddy Current array probe 802 on a pipe 804 covered with insulation material 806 and a metallic weather jacket 808 for corrosion under insulation inspection. The body of the array probe 802 is dimensioned and configured to cover a large area of the pipe 804, reducing the time of inspection and can be used to scan the pipe circumferentially as indicated by arrow 810.

Figure 8B:
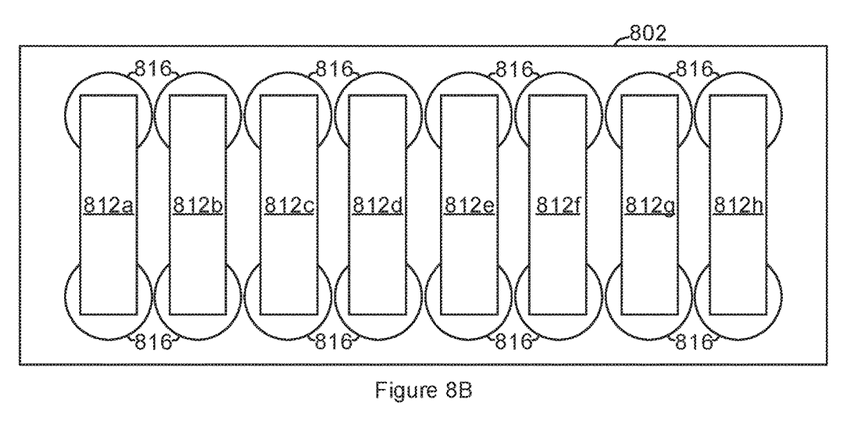
FIG. 8B shows an interior view of the array probe of FIG. 8A with multiple coil bundles without the transmitter coil.
Figure 8C:
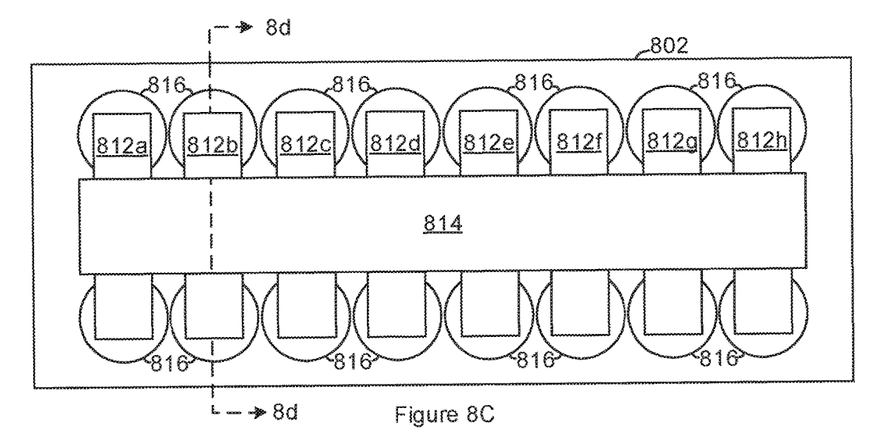
FIG. 8C shows an interior view of the array probe of FIG. 8B with the transmitter coil and FIG. 8D shows a detail of one coil bundle of the array probe of FIG. 8A.

FIG. 8B shows the interior of array probe 802 which includes multiple coil bundles. Eight equidistant U-shaped support cores 812a to 812h, collectively referred to as cores 812, are provided in array probe 802. Cores 812 are made of a material which can be ferromagnetic or not. Two dual-purpose coils 816 are mounted on each core 812. Transmitter coil 814 is omitted from this view but can be seen on FIG. 8C. FIG. 8C shows the interior of the array probe 802 including transmitter coil 814 which is wounded around all of the U-shaped support cores 812. All the dual-purpose coils 816 and the transmitter coil 814 are driven simultaneously.

Figure 8D:
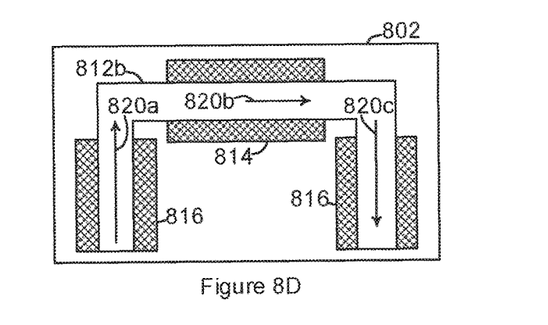

FIG. 8D is a cross-section view of the array probe 802 showing the polarity of each coil 814 and 816, which is set to obtain the magnetic field direction as indicated by the arrows 820a, 820b and 820c, collectively referred to as arrows 820.

Figure 9A:
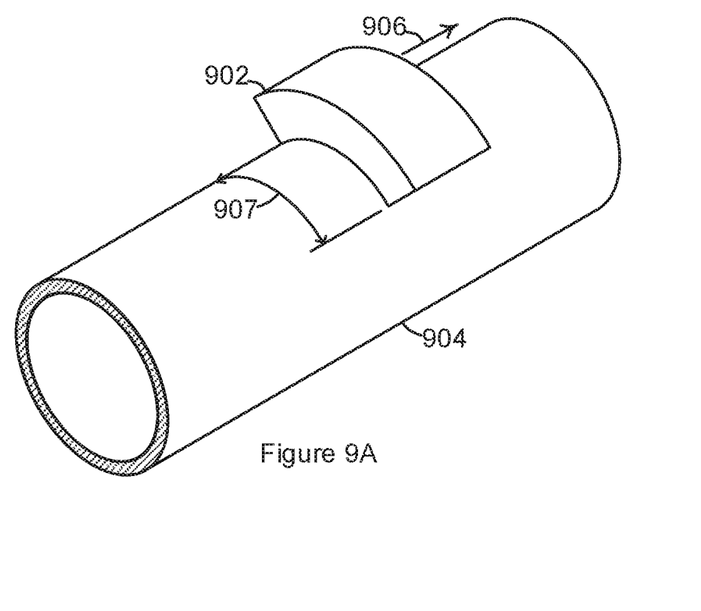
FIG. 9A shows another example array probe positioned on a pipe, the array probe being shaped to mate a circumference of the pipe
Figure 9B:
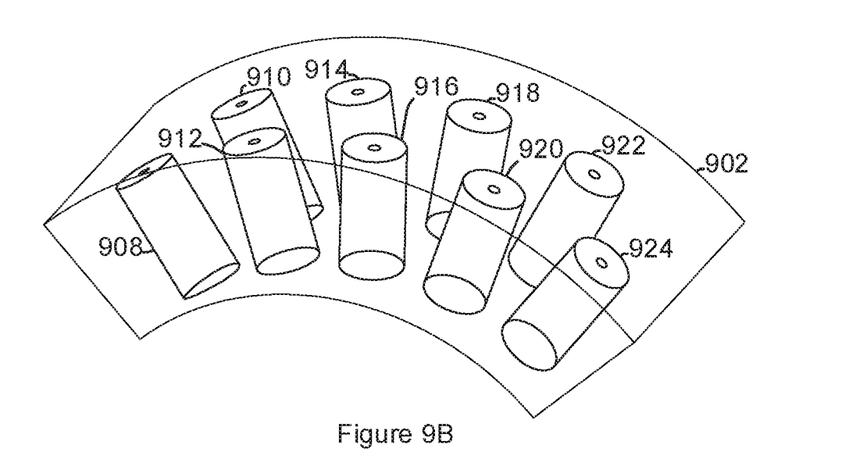
FIG. 9B shows the interior of the array probe of FIG. 9A with multiple coil bundles.

FIG. 9A shows an example Pulsed Eddy Current array probe 902, whose body is in direct contact with a pipe 904. The array probe 902 is dimensioned and configured to cover an angular section 907 of the pipe 904, reducing the time of inspection and can be used to scan along the longitudinal axis of the pipe 904 as indicated by arrow 906. In this example, the probe 902 covers a 90-degrees angular section of the pipe 904. The shape of the array probe 902 is adapted to follow the radius of curvature of the pipe 904. FIG. 9B shows the interior of the array probe 902 which includes nine coil bundles, namely dual-purpose coils 908 to 924 arranged in two rows. All the dual-purpose coils 908 to 924 are driven in a time multiplexing pattern, yielding a better resolution and reducing power consumption.

An example time multiplexing pattern would be driving dual-purpose coils 908, 914 and 920 during the first time-spaced instance, then driving dual-purpose coils 910, 916 and 922 during the second time-spaced instance and driving dual-purpose coils 912, 918 and 924 during the third and final time-spaced instance.

Figure 10A:
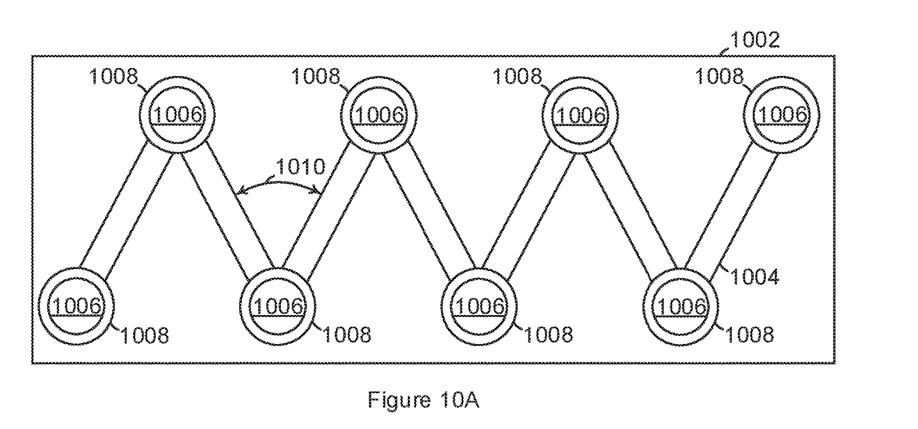
FIG. 10A shows a bottom view of the interior of another example array probe with a zigzag configuration for the coil bundles and FIG. 10B shows a side view of the array probe of FIG. 10A.

FIG. 10A shows an example Pulsed Eddy Current array probe 1002 including a ferromagnetic zigzag-shaped support 1004 with eight perpendicular legs 1006, one at each junction. A dual-purpose coil 1008 is mounted on each leg 1006. The angle 1010 of the zigzag junction is chosen depending on the targeted resolution.

Figure 10B:
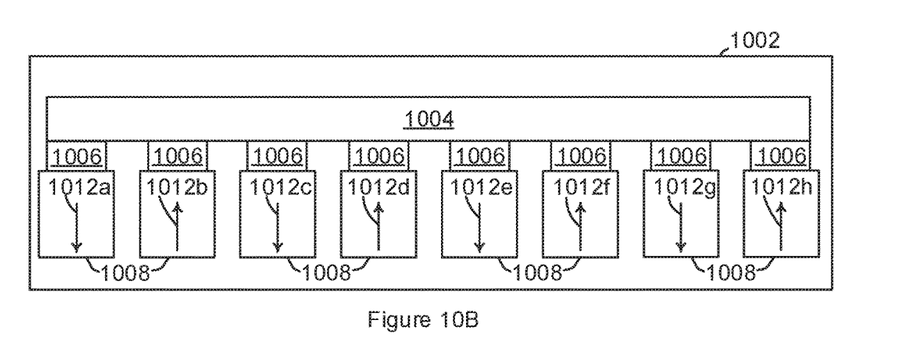

FIG. 10B is a side view of the array probe 1002 showing the polarity of each dual-purpose coil 1008, which is set to obtain the magnetic field direction as indicated by arrows 1012a to 1012h, collectively referred to as arrows 1012. All the dual-purpose coils 1008 are driven simultaneously.

EXAMPLE

An example embodiment is described based on the probe geometry shown in FIG. 5A and signal voltage shown on FIG. 2C. The object made of an electrically conductive material 502 which is being inspected is made of carbon steel and has a thickness of 10 mm. The corresponding exponential decay time constant can therefore be approximated to 10 ms. The insulation material 504 is non-ferromagnetic, non-conductive and has a thickness of 50 mm. The metallic weather jacket 506 is made of 1 mm thick aluminum. The flaw area this example targets to detect is equivalent to a circle of 50 mm diameter.

The probe 508 has three coils 510, 512 and 514 used as dual-purpose coils that are connected in series. The exponential decay time constant, 10 ms, is proportional to the time it takes to establish the magnetic field in the object 502. This time is also influenced by the time constant (L/R) of the three coils 510, 512 and 514 used as dual-purpose coils. In this example, a design choice was made to target the time constant (L/R) of the three coils 510, 512 and 514 to 10 ms. The design of this example is for a small probe and the coil size must be limited while allowing heat to dissipate to avoid probe overheating.

The design specifications are the following: a drive current of 1.5 A during the transmission phase 242, a target resistance of 10Ω for coils 510, 512 and 514 and a center-to-center distance 518 between coils 510 and 514 set at 1.5 times the thickness of the insulation material 504 to limit the area of magnetization on the object 502. The probe cable 528 is located on the left side of the probe instead of the top to minimize the probe height 526.

Each coil 510, 512 and 514 has a 20 mm outside diameter, a 50 mm length and 300 turns of 25 AWG copper wire. The U-Shaped support core 516 is made of ferrite, has a diameter of 16 mm, a center-to-center distance 518 between coils 510 and 514 of 75 mm and a distance 522 between the bottom of the probe 508 and the center of coil 512 of 60 mm. The series connection of the coils 510, 512 and 514 once assembled on the U-shaped support core 516 has a combined resistance of 10Ω and inductance of 100 mH, resulting in an overall time constant (L/R) of 10 ms.

The transmission phase 242 duration is set to 40 ms with an overdrive voltage 248 of 24 V and a plateau level voltage 250 of 1.5 A. The cut-off phase 244 duration is of the order of 1 ms and has a voltage inversion 252 of −120 V. The reception phase 246 duration is 40 ms and allows to obtain the eddy current-produced magnetic field from the object 502 as received by coils 510, 512 and 514.

Another example embodiment is described based on the probe geometry shown in FIG. 5A and signal voltage shown on FIG. 2C. The object made of an electrically conductive material 502 and which is being inspected is made of carbon steel and has a thickness of 5 mm. The corresponding exponential decay time constant can therefore be approximated to 3 ms. The insulation material 504 is non-ferromagnetic, non-conductive and has a thickness of 20 mm. The metallic weather jacket 506 is made of 0.6 mm thick aluminum. The flaw area this example targets to detect is equivalent to a circle of 30 mm diameter.

The probe 508 has three coils 510, 512 and 514 used as dual-purpose coils that are connected in series. The design of this example is for a small probe and the coil size must be limited while allowing heat to dissipate to avoid probe overheating.

The design specifications are the following: a drive current of 1.0 A during the transmission phase 242, a target resistance of 10Ω for coils 510, 512 and 514 and a center-to-center distance 518 between coils 510 and 514 set at 1.25 times the thickness of the insulation material 504 to limit the area of magnetization on the object 502.

Each coil 510, 512 and 514 has a 15 mm outside diameter, a 25 mm length and 400 turns of 25 AWG copper wire. The U-Shaped support core 516 is made of ferrite, has a diameter of 8 mm, a center-to-center distance 518 between coils 510 and 514 of 25 mm and a distance 522 between the bottom of the probe 508 and the center of coil 512 of 25 mm. The series connection of the coils 510, 512 and 514 once assembled on the U-shaped support core 516 has a combined resistance of 10Ω and inductance of 10 mH, resulting in an overall time constant (L/R) of 1 ms.

The transmission phase 242 duration is set to 12 ms with 10 V. The cut-off phase 244 duration is of the order of 0.1 ms and has a voltage inversion 252 of −100 V. The reception phase 246 duration is 12 ms and allows to obtain the eddy current-produced magnetic field from the object 502 as received by coils 510, 512 and 514.

The person skilled in the art will understand and appreciate the existence of variations, combinations, and equivalents of the specific embodiments, methods, and examples described herein. The invention should therefore not be limited by the above described embodiments, methods, and examples, but by all embodiments and methods within the scope and spirit of the invention.

We claim:

1. A Pulsed Eddy Current device for inspecting an object made of an electrically conductive material comprising:
   at least one dual-purpose coil, said at least one dual-purpose coil being configured to serve a dual purpose of producing a supplied magnetic field in said object and measuring a produced magnetic field emitted by said object;
   a transmitter circuit driving said at least one dual-purpose coil with an electrical signal, said transmitter circuit being connected to said dual-purpose coil via at least one electrical conductor, said electrical signal including a transmission phase, a cut-off phase and a reception phase, said transmitter circuit driving said dual-purpose coil to produce said supplied magnetic field and allowing penetration of said supplied magnetic field into said object during said transmission phase;
   a shut-off current circuit for said transmitter circuit for cutting-off a current in said dual-purpose coil during said cut-off phase of said electrical signal to produce a magnetic field variation which induces eddy currents in said object, said shut-off current circuit applying a voltage inversion on said dual-purpose coil; and
   a receiver circuit for reading said produced magnetic field from said at least one dual-purpose coil and for generating an inspection signal, said produced magnetic field being produced by said eddy currents in said object and emitted by said object during said reception phase of said electrical signal, said receiver circuit being connected to said dual-purpose coil via said at least one electrical conductor.

2. The Pulsed Eddy Current device as claimed in claim 1, wherein said transmission phase of said electrical signal contains an overdrive voltage phase and a plateau voltage phase.

3. The Pulsed Eddy Current device as claimed in claim 1, wherein shut-off current circuit includes at least one of a Transient Voltage Suppressor (TVS) and a resistor.

4. The Pulsed Eddy Current device as claimed in claim 1, further comprising a current controller circuit for controlling said transmitter circuit into providing said electrical signal.

5. The Pulsed Eddy Current device as claimed in claim 4, further comprising a current sensor for reading a current level in said dual-purpose coil and providing said current level to said current controller circuit for adjustment of said electrical signal provided by said transmitter circuit.

6. The Pulsed Eddy Current device as claimed in claim 5, wherein said current sensor is a shunt resistor.

7. The Pulsed Eddy Current device as claimed in claim 1, further comprising a surge protection circuit for protecting said receiver circuit against a signal representing said produced magnetic field, said surge protection circuit being adapted to prevent said signal from reaching said receiver circuit if said signal has a voltage value greater than a threshold value, said threshold value being lower than an absolute maximum input voltage of said receiver circuit.

8. The Pulsed Eddy Current device as claimed in claim 1, wherein said at least one dual-purpose coil has an overall time constant (L/R) of a same order of magnitude as a time constant of an approximated exponential decay of said supplied magnetic field in said object.

9. The Pulsed Eddy Current device as claimed in claim 1, further comprising at least one single-purpose transmitting coil, said at least one single-purpose transmitting coil serving a single purpose of producing an additional supplied magnetic field in said object, said additional supplied magnetic field being combined with said supplied magnetic field.

10. The Pulsed Eddy Current device as claimed in claim 1, further comprising at least one magnetic sensor, said at least one magnetic sensor serving a single purpose of measuring said produced magnetic field emitted by said object.

11. The Pulsed Eddy Current device as claimed in claim 1, further comprising a probe body, said at least one electrical conductor being sized to allow displacement of said probe body on said object remotely from said transmitter circuit and said receiver circuit, said probe body encasing said at least one dual-purpose coil and said shut-off current circuit.

12. The Pulsed Eddy Current device as claimed in claim 1, wherein a plurality of said at least one dual-purpose coil are assembled in an array, each one of said plurality measuring said produced magnetic field emitted by said object, said transmitter circuit driving each one of said plurality in one of a simultaneous mode and a time-multiplexed mode, wherein said transmitter circuit drives each of said at least one dual-purpose coil of said plurality simultaneously in said simultaneous mode and wherein said transmitter circuit drives selected ones of said at least one dual-purpose coil of said plurality simultaneously at each time instance in said time-multiplexed mode.

13. The Pulsed Eddy Current device as claimed in claim 12, wherein said plurality of said at least one dual-purpose coil are assembled on one of a U-shaped core, a three-pronged core, a matrix core and a zigzag-shaped core.

14. A method for inspecting an object made of an electrically conductive material by Pulsed Eddy Current measurement comprising:
   supplying a voltage on at least one dual-purpose coil by a transmitter circuit during a transmission phase of an electrical signal to drive said dual-purpose coil to produce a supplied magnetic field in said object;
   cutting-off a current in said at least one dual-purpose coil during a cut-off phase of said electrical signal to produce a magnetic field variation which induces eddy currents in said object, said cutting-off being carried out by applying a voltage inversion on said dual-purpose coil;
   receiving a produced magnetic field by said at least one dual-purpose coil during a reception phase of said electrical signal, said produced magnetic field being produced by said eddy currents in said object and emitted by said object; and
   outputting an inspection signal by a receiver circuit, said inspection signal being representative of said produced magnetic field in said object received by said at least one dual-purpose coil.

15. The method as claimed in claim 14, further comprising reading a current level in said dual-purpose coil and adjusting said electrical signal using said current level.

* * * * *